United States Patent [19]

Shoor

[11] 4,256,106
[45] Mar. 17, 1981

[54] RESEALABLE DEVICE

[75] Inventor: Bernard A. Shoor, New York, N.Y.

[73] Assignee: Becton, Dickinson and Company, Paramus, N.J.

[21] Appl. No.: 34,856

[22] Filed: Apr. 30, 1979

[51] Int. Cl.³ .............................................. A61M 3/00
[52] U.S. Cl. .................. 128/247; 251/149.1; 251/341
[58] Field of Search ............... 128/247, 214.2; 251/4, 251/149.1, 341, 342

[56] References Cited

U.S. PATENT DOCUMENTS

| 2,706,101 | 4/1955 | Cantor | 251/4 |
| 3,977,403 | 8/1976 | Patel | 128/247 X |
| 4,056,116 | 11/1977 | Carter et al. | 128/214.2 X |

Primary Examiner—John D. Yasko
Attorney, Agent, or Firm—Louis E. Marn; Elliot M. Olstein

[57] ABSTRACT

A device, particularly suitable as a connector, comprised of a housing having an open end closed by an elastomeric membrane. The membrane has at least one preformed opening, which is normally closed and which is opened upon deformation of the membrane, with the opening being reclosed upon release of the deformation force. The housing interior may include means for applying a deformation force to the membrane to open the opening therein.

17 Claims, 6 Drawing Figures

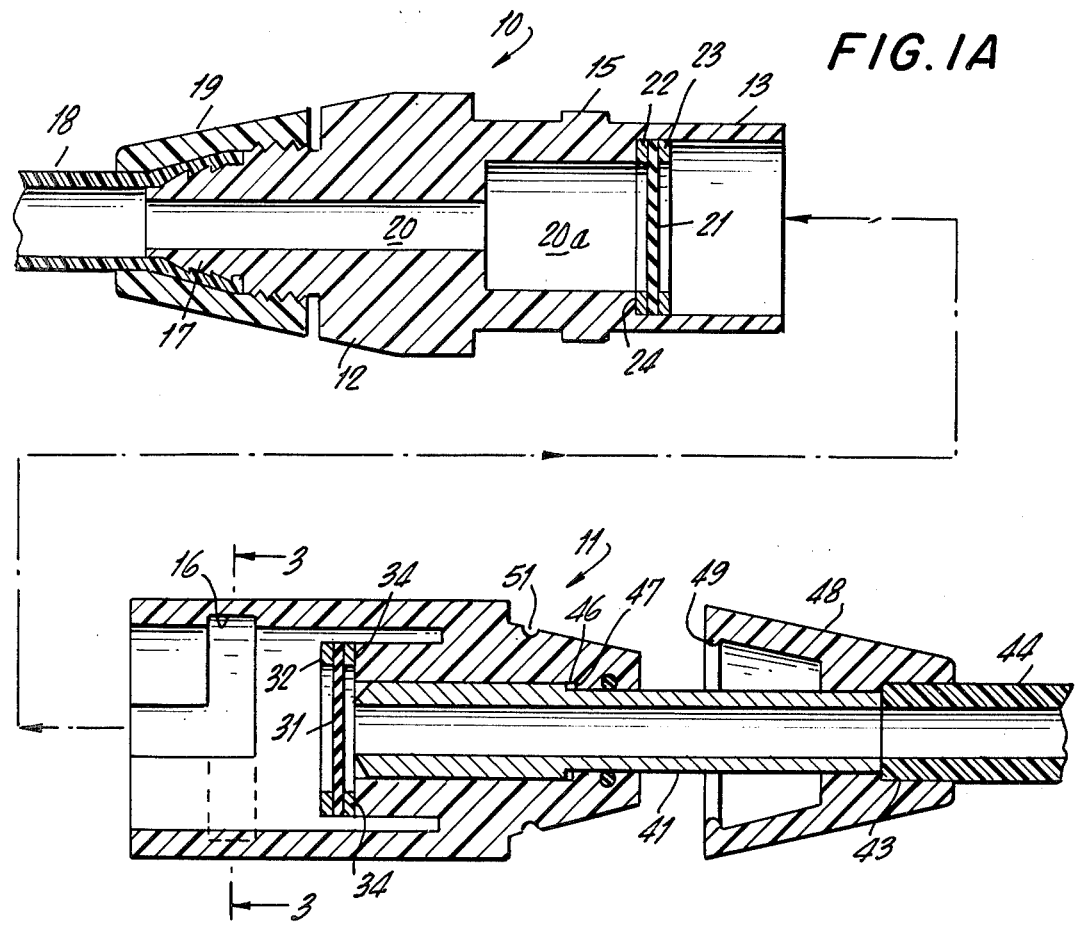

RESEALABLE DEVICE

This invention relates to a device having a closure which is capable of being opened and resealed and more particularly to a device particularly suitable for use as a connector.

For many applications there is a need for a device which is capable of being easily opened and resealed. Thus, for example, such a device has particular utility as a connector wherein it is necessary to open and close the connecting end upon connection to and disconnection from another connector.

In many cases, such connectors are employed for connection and disconnection wherein it is necessary to maintain sterile integrity. Thus, for example, as a result of recent advances, there is currently available an implantable, bacteriologically-safe peritoneal-dialysis catheter for peritoneal dialysis. Such a development makes possible home peritoneal dialysis, which involves connection and disconnection of the catheter to a source of dialysis fluid under sterile conditions. As a result, there is a need for new and improved terminal connectors which permit connection and disconnection, while maintaining sterile conditions.

In accordance with one aspect of the present invention, there is provided a device comprised of a housing having an open end, with the open end being closed by a deformable membrane which includes at least one preformed opening which is normally closed and which opening is opened upon application of a deformation force to the membrane, with the opening being reclosed upon release of the deformation force. It is to be understood that the term preformed opening refers to the membrane including an opening which is open when the membrane is deformed and which is closed when the membrane is in its normal undeformed state.

In accordance with another aspect of the present invention, there is provided a device comprised of a housing having an open end, with the open end being closed by a deformable membrane which includes at least one preformed opening which is normally closed and which opening is opened upon application of a deformation force to the membrane, with the opening being reclosed upon release of the deformation force, with the housing interior including a deforming means for releasably applying the deformation force to the membrane to effect such opening and reclosing.

The device of the present invention has particular use as a connector for the transfer of material, with the open end thereof being adapted to being connected to a mating connector. The connector has particular use as a sterile connector wherein the deformable membrane maintains the sterile integrity of the housing interior.

In accordance with a preferred aspect of the present invention, there is provided a pair of mating terminal connectors which are adapted to being connected to each other. One of the connectors is comprised of a housing have a sterile interior which is adapted to being connected to a suitable flow line or device and an open connecting end, adapted to being connected to its mating connector, with the open end being closed by a deformable membrane having a preformed opening as hereinabove described.

The other connector of the pair is comprised of a housing having a sterile interior which is adapted to being connected to a flow line or device, and an open connecting end adapted to being connected to its mating connector. The open connecting end is preferably closed by a deformable membrane having a preformed opening of the type hereinabove described to thereby maintain the sterile integrity of the housing interior. Alternatively, the other connector could include other suitable closure means which can be pierced or otherwise opened to establish communication with its interior.

One of the pair of connectors includes a deformation means, which upon connection of the connector pair is capable of applying a releasable deformation force to both membranes to open the preformed openings therein to establish communication between the pair of connectors. If one of the connectors includes a closure without a preformed opening such deformation means is also capable of opening such closure; e.g., by piercing the closure.

In accordance with a particularly preferred embodiment, each of the connectors is closed by a membrane with a preformed opening, of the type hereinabove described, and upon connection of the connector pair such membranes either contact each other or are in close proximity to each other. The deformation means applies a deformation force against the interior of one of the membranes and is moved to stretch both membranes to open such preformed openings. In such stretched position, the membranes are preferably in contact with each other in at least the areas thereof around the openings therein.

The deforming means is preferably in the form of a movable plunger having a hollow interior defining a flow passage which is connected to an associated flow line, with the plunger having an open end which contacts the interior of the membrane of one of the connectors to stretch the membranes of both connectors in a contacting relationship such that the open end of the plunger is in communication with the open portions of the membranes. With the membrane openings opened, the plunger is in contact with the interior of the membrane of one connector, whereby fluid can flow from the open end of the plunger through the openings in both membranes into the interior of the mating connector for subsequent flow through associated flow lines.

The stretchable resilient membrane is provided with the preformed opening or openings in the stretch position, whereby the opening is closed upon release of the stretching force. Such holes are preferably formed by burning; e.g., with a laser. The opening may take any one of a wide variety of forms such as holes, slits, etc. One form which has been found to be particularly suitable is a narrow slit having holes at the axial ends thereof to prevent further tearing and extension of the slit.

The membrane is preferably formed from natural rubber or a segmented polyether, polyurethane elastomer (LYCRA). It is to be understood, however, that the use of other elastomeric materials is possible within the spirit and scope of the invention.

In use, the connectors are connected to each other (the connectors preferably form a hermetic connection), and in the connected position (prior to opening of the preformed openings) the outer surfaces of the membranes are sterilized. Such sterilization can be accomplished by application of a suitable sterilizing fluid to the outer membrane surfaces, with the contact between the fluid and surfaces being maintained for a time period sufficient to effect sterilization. The sterilization is accomplished with the connectors connected to each other to minimize the chances of contamination from the external environment. Alternatively, sterilization could be accomplished by other procedures; e.g., by heat. After a sufficient period of time to effect sterilization, the deforming means is advanced to stretch the membranes of each connector into a sealing relationship with each other in at least the area of the openings therein, with such stretching also opening the preformed openings. The sealing of the membranes to each other in this manner traps the sterilizing fluid and minimizes the chances of sterilizing fluid entering the open fluid flow path. In addition, such sealing relationship prevents communication between the exterior surfaces of the membranes which are sterilized by a user and the presterilized internal portions of the connectors and associated equipment to thereby further reduce the risk of contamination.

The invention will be further described with respect to the accompanying drawings, wherein:

FIGS. 1A–1C illustrate a preferred embodiment of the invention;

FIG. 3 is a section along line 3—3 of FIG. 1A.

Figure 1B:
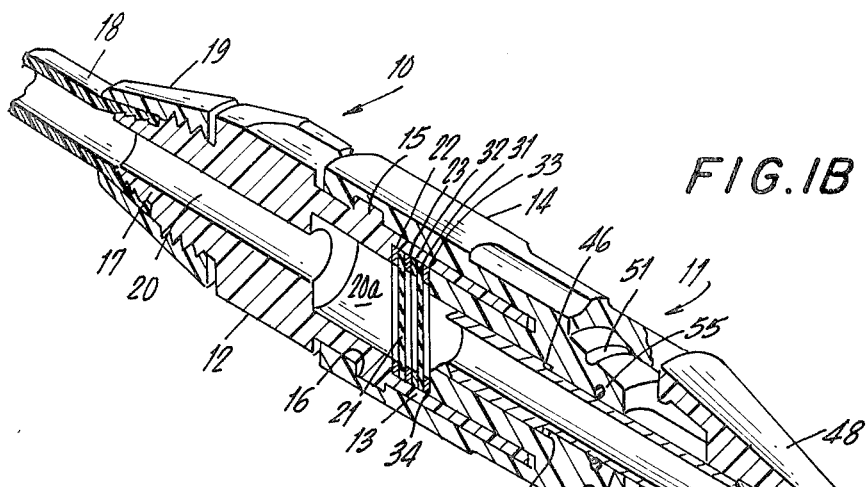

It is to be understood, however, that the scope of the invention is not to be limited to such an embodiment.

Referring now to the drawings, there is shown a pair of mating terminal connectors 10 and 11, which can be constructed, for example, from a suitable plastic. Terminal connector 10 is comprised of a main tubular body portion 12, which at the open connecting end thereof has an elongated neck portion 13 which is adapted to be telescopically received within the interior of the open connecting end of the tubular main body portion 14 of connector 11. The exterior of the neck portion 13 is provided with suitable ridges or pins 15 to be received in corresponding grooves 16 in the interior of connector 11 to provide a bayonet-lock type connection between the two connectors. The mating connection is preferably designed in a manner such as to provide a hermetic seal between the connectors.

The main body portion 12 of connector 10 opposite to the connecting end thereof includes an elongated portion 17, which is inserted, for example, into a catheter 18 which is to receive sterilized fluid. The catheter 18 may be maintained in position by suitable fastening means such as threaded connector 19 having interior threads which are received by corresponding threads on the exterior of elongated portion 17.

The elongated portion 17 includes an axial interior channel 20, in fluid flow communication with the interior of catheter 18, and which opens into an enlarged chamber 20a within the main body portion 12 of connector 10.

The open connecting end of connector 10 is sealed by a membrane or diaphragm assembly comprised of an elastomeric membrane 21 sandwiched between rings 22 and 23 to provide a unified assembly. The membrane assembly is appropriately sealed to an annular shoulder 24 to effectively close and seal the open end of connector 10 to thereby prevent contamination of the sterile interior portions and associated flow equipment. The membrane assembly is recessed within the interior of the connector 10 to prevent contact therewith during the handling of the connector. Thus, the main body portion functions as a shield to protect the membrane 21.

The membrane 21 is provided with one or more preformed openings which are normally closed, and which are opened by stretching of the membrane, and which are resealed when the stretching force is released. The membrane is preferably formed from a material and constructed in a manner such that there is a disproportionate increase in the open area of the preformed opening as compared to the distance over which the membrane is stretched. The membrane preferably provides a gas, liquid and bacterial tight seal so as to prevent entry of contaminants into the connector and associated equipment. The terminal connector 10 is preferably closed by a suitable cap when not being used.

The open connecting end of connector 11 is also closed by a membrane or diaphragm assembly comprised of an elastomeric membrane 31 sandwiched between a pair of rings 32 and 33. The membrane assembly preferably provides a liquid, gas and bacterial tight seal and is appropriately fastened to an interior shoulder 34 within the connector interior. As hereinabove described with respect to the membrane closing the open end of connector 10, the membrane 31 is provided with one or more preformed openings which are normally closed, and which can be opened upon stretching of the membrane. The membranes 31 and 21 are positioned in their respective connectors in a manner such that when connectors 10 and 11 are connected to each other the membranes are in close proximity to each other whereby the membranes can be simultaneously stretched for opening the preformed openings therein, with the membranes preferably being in a sealing relationship with each other in at least the area surrounding the openings, as hereinafter described.

The connector 11 is provided with a stretching assembly in the form of a hollow plunger 41 having an internal passage 42 which includes an enlarged portion 43 into which suitable tubing 44 is bonded, with such tubing being in fluid flow communication with a source of sterilized fluid. The plunger extends into the hollow interior of the connector 11 through a bore 45 with the external surface of the plunger being in a sliding sealing fit with the internal surface of bore 45 which includes o-ring 55 to prevent leakage of fluid from the interior of connector 11. The forward portion of the plunger 41 includes an external shoulder portion 46 which abuts against a shoulder 47 within the interior of connector 11 to prevent withdrawal of the forward end of the plunger from the connector. The rearward end of the plunger 41 is provided with an enlarged head portion 48 which includes a circular bead portion 49 which is adapted to fit into a circular groove 51 on the external rear surface of connector 11 to lock the plunger in its advanced position, as hereinafter described.

In using the connector assembly, for example, for peritoneal dialysis, the reusable connector 10 is connected to an indwelling catheter, and contamination of the internal portions of the connector and associated catheter is prevented by membrane 21 which seals the open end of connector 10. In addition, such membrane prevents any fluid which is in connector 10 from flowing out of the connector.

The connector 11 is connected to a source of dialysis fluid through its associated tubing 44. The open end of connector 11 is sealed by membrane 31 to prevent contamination of the interior of connector 11 and its associated equipment. The membrane 31 also prevents dialysis fluid contained in the interior of connector 11 and associated tubing from being released from the connector.

Prior to connecting connectors 10 and 11, sterilizing fluid, e.g., polyvinylpyrrolidone Iodide such as sold under the mark Betadine, is placed on the external surfaces of membranes 21 and 31. Subsequently, connectors 10 and 11 are connected to each other in a sealing relationship through the bayonet-lock type connection whereby the sterilizing fluid is trapped between the external surfaces of membranes 21 and 31 and in sterilizing contact therewith. As should be apparent, in view of the connection between the connectors, the external surfaces of the membranes are sterilized without the risk of contamination from the external environment.

After contact between the sterilizing fluid and the external surfaces of the membranes has been maintained for a time sufficient to effect sterilization, plunger 41 is advanced against the internal surface of membrane 31 and the advancement continued until the plunger head is locked to the rear external surface of connector 11 through the snap-fit connection between groove 51 and corresponding bead 40. The forward advancement of plunger 41 stretches both membrane 21 and 31 to open the preformed openings, with the external surfaces of the membranes being moved into a sealing relationship with each other in at least the area of the openings. The open end of plunger 41 touches the interior portion of membrane 31 and in this manner there is essentially no contact between the presterilized portions of the connector and associated equipment, and the exterior portions of the membranes which are sterilized by a user immediately prior to use of the connectors. In this manner, any risk of contamination from the external surface portions of the membrane has been significantly reduced.

In addition, as a result of the stretched sealing relationship between the membranes 21 and 31, the sterilizing fluid is trapped by such membranes to minimize entry of sterilizing fluid into the main fluid flow path. The membrane 31 may be provided with suitable additional holes, which do not have corresponding holes in membrane 21, which would permit drainage of sterilizing fluid through the membrane into a pocket formed between the advanced plunger 41 and the internal portions of the connected assembly; not FIG. 1C wherein such pockets are indicated by reference numeral 52. Such holes, however, could be eliminated.

Figure 1C:
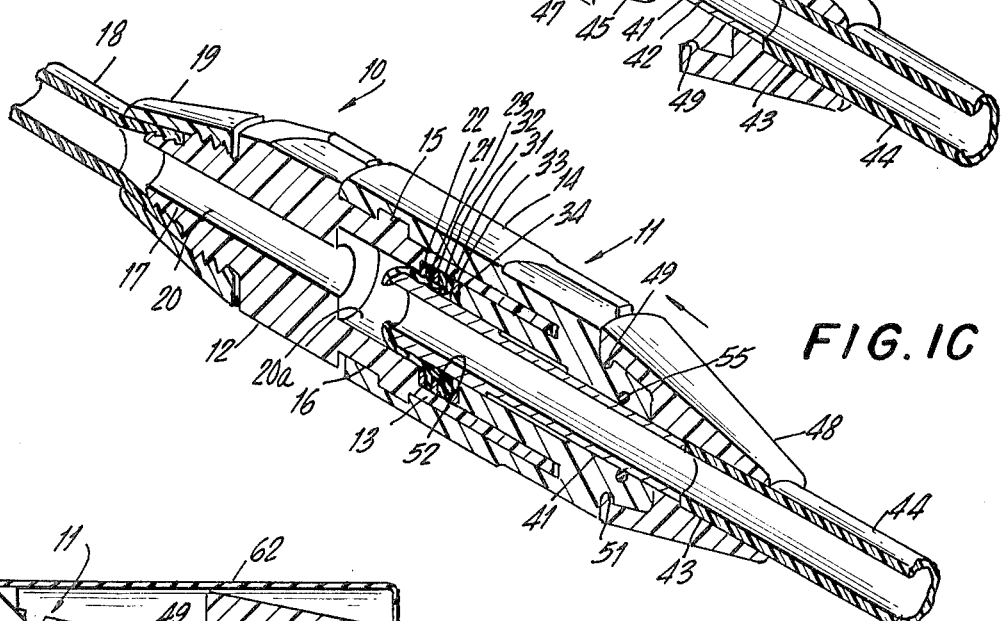

As should be apparent from FIG. 1C, dialysis fluid can now flow through tubing 44, internal plunger passage 42 and into the connector 10 for introduction into the peritoneal cavity through associated catheter 18. In addition, such fluid flows essentially only through portions of the connector and associated equipment which have been presterilized by other than the user thereby minimizing the risk of contamination by inadequate user sterilization.

Upon disconnection of the connectors 10 and 11, the stretching force on membrane 21 is released, whereby the membrane resumes its normal position in which the opening or openings therein is closed to thereby maintain the sterile integrity of the interior portions thereof and to prevent leakage of any fluid therefrom.

Alternatively, the plunger can be withdrawn prior to disconnection to release the stretching force and close the openings prior to disconnection.

The connector 11 can be a single use connector, with such connector and associated equipment (for example, tubing and bag for dialysis fluid) being included in a presterilized package. Such connector and associated equipment can be removed from the sterilized package and connected to the reusable mating connector 10 for use as hereinabove described.

Figure 2A:
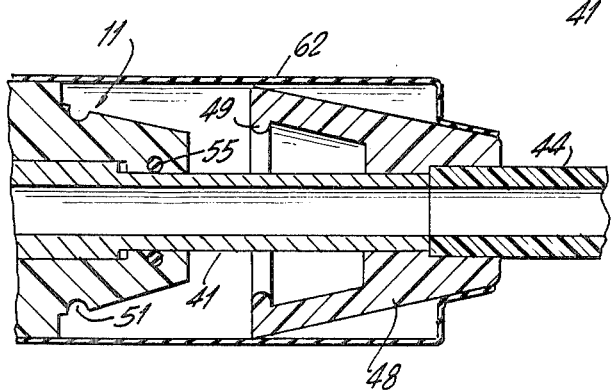
FIGS. 2A–2B illustrate a modification of the embodiment of FIGS. 1A–1C.
Figure 2B:
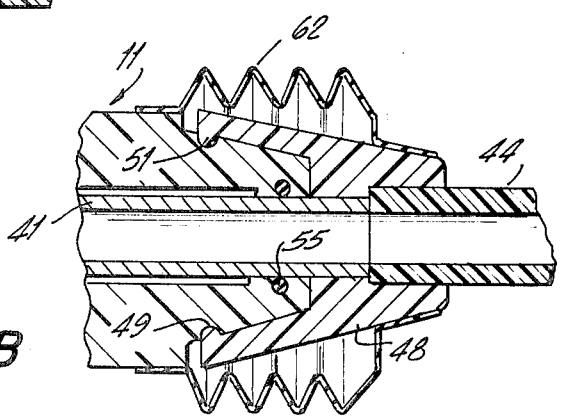

It is also possible to employ connector 11 for more than a single use; i.e., as a reusable connector. Thus, for example, in dialysis it is possible to use only a portion of the fluid in a connected bag, followed by disconnection and reconnection at a later time to utilize remaining fluid. In such use, the plunger would be withdrawn prior to disconnection, with such plunger withdrawal reclosing the openings in the deformable membrane in both mating connectors, whereby sterile integrity is maintained after disconnection. In employing the connector including the plunger element as a reusable connector, means should be provided for insuring the sterility of the portions of the plunger which are normally external of the connector interior; i.e., exposed to ambient environment, and which enter the sterile interior upon advancement of the plunger. Such sterility can be maintained, for example, by providing a protective cover for the portions of the plunger which are exterior of the connector in the withdrawn position. Thus, for example, as shown in FIGS. 2A and 2B, which illustrate only a portion of the connector including the plunger element, the plunger is provided with a cover 62 which is sealed at one end to plunger head 41 and at the other end to the connector 11. The cover 62 is formed of a suitable deformable and resilient material, such as an elastomeric material, and such cover effectively seals the plunger from the atmosphere. Upon advancement of the plunger (FIG. 2B), the cover 62 is deformed into a bellows-like shape and upon retraction of the plunger, the cover resumes the shape shown in FIG. 2A. In this manner, the sterile integrity of the exterior portions of the plunger which enter and are withdrawn from the sterile interior of the connector is maintained. It is to be understood that the cover could take a form other than that particularly shown. It may also be possible, in some cases, to reuse the connector including the plunger element without providing a cover. Thus, for example, in some cases it may be possible to provide an appropriate wiping action to the plunger exterior (by an o-ring) to prevent contaminants from entering the connector interior when advancing the plunger.

The exterior surfaces of the stretchable membranes are sterilized subsequent to connection of the mating connectors. Although such sterilization has been particularly described with reference to the use of a sterilizing liquid, it is to be understood that such sterilization could be accomplished in other ways, for example, by heat.

Although the connectors have been described with particular referene to peritoneal dialysis with the reusable connector being attached to an indwelling catheter, it is to be understood that the connectors are also suitable for other uses where sterile connection and disconnection is desired; for example, for transfer of intravenous fluid, extracorporeal blood lines, plasma fractionation, pharmaceutical preparations, etc. The above uses and others should be apparent to those skilled in the art. The connectors may be employed for transferring a wide variety of materials (solids, gases, liquids, preferably liquids or gases).

Similarly, the connectors hereinabove described can be modified within the spirit and scope of the invention. Thus, for example, the connector 11, which includes the stretching means in the form of a plunger can be employed as a reusable connector and attached to the catheter 18.

As a further alternative, the connectors can be employed for uses where sterile conditions are not required. Thus, in such uses, it is not necessary to provide sterile interiors.

As another alternative, connector 11 could have its open connecting end closed by means other than a stretchable resilient membrane having at least one preformed opening. Thus, for example, the open end could be closed with a pierceable or rupturable cover, with such cover being opened by advancement of the plunger or other movable deformation means, with the plunger subsequently stretching the membrane of mating connector 10 to open the preformed opening therein and establish material flow communication between the connectors. In such case, connector 11 would not be reusable.

Although the preferred embodiment has been described with particular reference to connectors, the principles of the present invention are applicable to other uses. Thus, for example, the resilient deformable membrane having a preformed opening can be employed as a seal for a housing used as a container for materials which are to be dispensed from the housing, with the housing interior including a deforming means to apply a releasable stretching force to the membrane to open and reclose the membrane in the manner hereinabove described. Thus, by providing a deforming means in the form of a hollow plunger having an open end for contacting and stretching the membrane, with the open end of the plunger in communication with the membrane opening in the stretched position, the material in the container can enter the interior of the plunger through a suitable opening or openings and be dispensed through the plunger interior and opening in the stretched membrane. Upon retracting the plunger, the opening or openings in the membrane are reclosed to thereby close the housing and prevent material flow therefrom.

As should be apparent, in using the present invention as a sterile connector assembly the risk of contamination is minimized in that the interface between presterilized portions and the areas which were not presterilized; i.e., the exterior portions of the membranes, are minimized, in that the sealing relationship between the membranes essentially isolates such surfaces from the presterilized portions of the connector assembly. In addition, the sterilization of such surfaces by the user is conducted after locking of the connectors to thereby further reduce contamination. In addition, by providing the membranes well recessed within the connector, skin contact with such surfaces during handling of the connector is eliminated. Furthermore, closing of the connector 10 which is connected to the fluid flow path to the peritoneal cavity is automatic, whereby if the two connectors are accidentally disconnected, the open end of connector 10 is automatically sealed. In addition, accidental entry of contaminants as a result of pressure differences is avoided.

Numerous modifications and variations of the present invention are possible in light of the above teachings and, therefore, within the scope of the appended claims, the invention may be practiced otherwise than as particularly described.

I claim:

1. A device, comprising:
    a housing having an open end and defining a material receiving interior;
    a resilient membrane closing and sealing the open end of the housing, said membrane including at least one preformed opening which is normally closed and which is opened upon stretching the membrane, with the opening being closed upon release of the stretching force; and said housing including an integral movable stretching means within the housing for applying a releasable stretching force to the membrane to open and close the at least one preformed opening in the membrane, whereby material can be transferred through the opening on application of the stretching force and material transfer prevented by release of the stretching force.

2. The device of claim 1 wherein the movable stretching means is in the form of a hollow plunger having an open end to apply the releasable stretching force.

3. A terminal connector, comprising:
    a housing defining an interior for material transfer, said housing including an open connecting end and a material transfer opening; a resilient membrane closing and sealing the interior from the open connecting end, said membrane including at least one preformed opening which is normally closed and which is opened upon stretching the membrane, with the opening being closed upon release of the stretching force; and said housing including an integral movable deforming means within the housing for applying a releasable stretching force to the resilient membrane, whereby the movable deforming means can be moved to deform the membrane and open the preformed opening for material transfer communication between the housing interior and a mating connector connected to the open connecting end.

4. The terminal connector of claim 3 wherein the terminal connector is a sterile connector having a sterile interior.

5. The terminal connector of claim 4 wherein the resilient membrane is recessed within the housing from the open connecting end.

6. The terminal connector of claim 5 wherein the open connecting end has means for forming a hermetic seal with a mating connector.

7. The terminal connector of claim 3 wherein the movable stretching means is in the form of a hollow plunger having an open end to apply the releasable stretching force and and an opposite end which includes said material transfer opening for said housing whereby material is transferred between the mating connector and the material transfer opening through said hollow plunger.

8. A connector assembly, comprising:
    a pair of terminal connectors for connection to each other, each of said connectors including a housing defining a material transfer interior, each of said housings including an open connecting end, each of said housings including a material transfer opening, each of said housings including an openable closure means for closing the housing interior from the open connecting end, at least one of said closure means being comprised of a resilient membrane including at least one preformed opening which is normally closed and which is opened upon stretching the membrane, with the opening being closed upon release of the stretching force, one of said pair of connectors including a movable stretching means within the housing interior, said movable stretching means, after connection of the connector pair being movable to apply a releasable stretching force to at least the at least one resilient membrane to open the at least one preformed opening therein.

9. The assembly of claim 8 wherein the closure means of both connectors is comprised of said resilient membrane.

10. The assembly of claim 9 wherein the resilient membranes are recessed within the housing from the open connecting ends.

11. The assembly of claim 10 wherein the connector assembly is a sterile connector assembly having sterile housing interiors.

12. The assembly of claim 11 wherein the movable stretching means is comprised of a plunger which stretches both membranes by application of a stretching force to the interior surface of one membrane.

13. The assembly of claim 12 wherein the stretching means stretches the membranes with the membranes in contact with each other in at least the areas thereof having the at least one opening therein.

14. The assembly of claim 13 wherein the plunger includes an internal flow passage adapted to being connected to a flow line, said plunger including an open end which is in communication with the openings in the membranes when the plunger stretches the membranes.

15. A terminal connector, comprising:
a housing, said housing including an open connecting end adapted for connection to a mating connector, and an interior bore recessed inwardly from the open connecting end;
a resilient membrane closing and sealing the bore from the open connecting end, said membrane including at least one preformed opening which is normally closed and which is opened upon stretching the membrane, with the opening being closed upon release of a stretching force;
a plunger reciprocally movable in said bore into and out of stretching engagement with said membrane, said plunger extending through said bore outwardly of said housing, said plunger including an interior passage having a first open end which is in communication with openings in the membrane when the plunger stretches the membrane, and a second open end adapted to being connected to a flow line, whereby upon stretching of the membrane material flows through openings in the membrane through the passage in the plunger.

16. The connector of claim 15 wherein the terminal connector is a sterile connector having a sterile interior portion sealed by said membrane.

17. The terminal connector of claim 16 wherein the open connecting end has means for forming a hermetic seal with a mating connector.

* * * * *